United States Patent
Schmid et al.

(10) Patent No.: US 6,533,857 B1
(45) Date of Patent: Mar. 18, 2003

(54) GLOSS PIGMENTS COMPRISING AN ABSORBENT LOW-REFRACTIVE COATING

(75) Inventors: Raimund Schmid, Neustadt (DE); Arno Böhm, Mannheim (DE); Oliver Seeger, Mannheim (DE); Norbert Mronga, Dossenheim (DE); Thorsten Clemens, Hochdorf-Assenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/069,666

(22) PCT Filed: Aug. 23, 2000

(86) PCT No.: PCT/EP00/08217

§ 371 (c)(1),
(2), (4) Date: Feb. 28, 2002

(87) PCT Pub. No.: WO01/16236

PCT Pub. Date: Mar. 8, 2001

(30) Foreign Application Priority Data

Aug. 31, 1999 (DE) .......................................... 199 41 253

(51) Int. Cl.[7] .................................................. C09C 1/62
(52) U.S. Cl. ................. 106/403; 106/417; 106/418; 106/431; 106/436; 106/439; 106/440; 106/441; 106/450; 106/453; 106/456
(58) Field of Search ............................ 106/417, 403, 106/418, 431, 436, 439, 450, 453, 456, 440, 441

(56) References Cited

U.S. PATENT DOCUMENTS

| | | |
|---|---|---|
| 3,438,796 A | 4/1969 | Hanke |
| 4,434,010 A | 2/1984 | Ash |
| 5,958,125 A | * 9/1999 | Schmid et al. ............... 106/415 |

FOREIGN PATENT DOCUMENTS

| | | |
|---|---|---|
| DE | 41 40 295 | 6/1993 |
| DE | 197 46 067 | 10/1997 |
| DE | 198 08 657 | 3/1998 |
| DE | 198 22 046 | 5/1998 |
| EP | 668 329 | 2/1995 |
| EP | 708 154 | 4/1996 |
| EP | 0 753 545 | 1/1997 |
| EP | 0 940 451 | 9/1999 |
| EP | 0 959 109 | 11/1999 |
| WO | 93 08237 | 4/1993 |
| WO | 96/34917 | 11/1996 |

OTHER PUBLICATIONS

Raimund Schmid et al.: Luster pigments with optically variable properties European Coatings Journal, vol. 7–8, pp. 702–705.

* cited by examiner

Primary Examiner—Mark L. Bell
Assistant Examiner—Shalie Manlove
(74) Attorney, Agent, or Firm—Oblon, Spivak, McClelland, Maier & Neustadt, P.C.

(57) ABSTRACT

Luster pigments based on multiply coated reflecting platelet-shaped substrates and comprising at least one layer packet comprising A) a low refractive coating which selectively absorbs visible light and B) a reflective coating which is at least partially transparent to visible light and also, if desired, C) an outer protective layer.

9 Claims, No Drawings

GLOSS PIGMENTS COMPRISING AN ABSORBENT LOW-REFRACTIVE COATING

The present invention relates to novel luster pigments based on multiply coated reflecting platelet-shaped substrates and comprising at least one layer packet comprising A) a low refractive coating which selectively absorbs visible light and B) a reflective coating which is at least partially transparent to visible light and also, if desired, C) an outer protective layer.

The invention further relates to the use of these luster pigments for coloring paints, inks, including printing inks, plastics, glasses, ceramic products and decorative cosmetic preparations.

Luster or effect pigments are used in many sectors of industry, for example in automotive coatings, decorative coating, plastics coloration, paints, printing inks, especially security printing inks, and cosmetics.

Their optical effect is based on the directed reflection of light at predominantly sheetlike, mutually parallel-oriented, metallic or strongly refractive pigment particles. Depending on the composition of the pigment platelets, interference, reflection and absorption phenomena create angle-dependent color and lightness effects.

Particular interest pertains to goniochromatic luster pigments which exhibit an angle-dependent color change between two or more intensive interference colors and hence an attractive color play. These pigments typically have a light-reflecting platelet-shaped core which is coated with alternating low and high refractive layers.

An overview of goniochromatic luster pigments is given in European Coatings Journal 7–8, page 702–705 (1997). Details relating to the goniochromatic luster pigments described therein and others are described in U.S. Pat. No. 3,438,796, U.S. Pat. No. 4,434,010, EP-A-668 329, WO-A-96/34917, EP-A-708 154, EP-A-753 545 and DE-A-197 46 067 and prior German Patent Applications 198 08 657.1 and 198 22 046.4.

A common feature of all known goniochromatic luster pigments is a colorless low refractive layer, which is frequently referred to as a dielectric layer, which is responsible for the angle-dependent color of the pigments and whose delicate interference colors are enhanced by the combination with high refractive and optionally absorbing layers. In use, the color play of these pigments is customarily modified by blending with other colorants to match the particular coloristic requirements and the personal taste of the user. Since color sensation and personal taste are very individual, however, there is still a need for new effects which cannot always be satisfied by combining known colorants.

It is an object of the present invention to provide further goniochromatic luster pigments which exhibit new coloristic effects and have advantageous application properties.

We have found that this object is achieved by the goniochromatic luster pigments defined at the beginning.

The invention further provides for the use of the luster pigments according to the invention for coloring paints, inks, including printing inks, plastics, glasses, ceramic products and decorative cosmetic preparations.

The luster pigments of the invention are based on multiply coated reflecting platelet-shaped substrates comprising a low refractive coating (A) which selectively absorbs visible light, in combination with a reflective coating (B) which is at least partially transparent to visible light.

Useful substrate materials for the luster pigments of the invention include all platelet-shaped materials which reflect perpendicularly incident light completely or partially (typically at not less than 10%). These materials are generally high refractive and customarily have a refractive index of generally $\geq 2$, preferably $\geq 2.4$; they can be opaque, semiopaque or transparent and also colored in reflected or transmitted light.

One group of useful substrate materials are metal platelets. Any metallic effect pigment metals and alloys may be used, for example steel, copper and its alloys such as brass and bronzes and especially aluminum and its alloys such as aluminum bronze. Preference is given to aluminum flakes, which are simple to produce by stamping out of aluminum foil or according to common atomizing and grinding techniques, and it is possible to use commercially available products whose surface, however, should be substantially free of greases or similar coatings and may be passivated, ie stablilized with regard to water in particular.

The metallic substrate particles may if desired already be coated with high refractive metal compounds such as-high refractive metal oxide, metal nitride or metal sulfide, especially for example iron oxide or titanium oxide, and therefore already possess a (weak) self-color due to interference effects with or without absorption (Paliocrom®, BASF). However, this coating should not be too thick (from about 5 to 150 nm) in order that the substrate particles may retain their metallic coloristics. Furthermore, the metallic substrate particles may also be coated with magnetic materials such as iron, cobalt, nickel or γ-iron(III) oxide and hence be magnetizable.

A further group of suitable substrate materials are nonmetallic platelets which are inherently high refractive or inherently only low refractive and therefore provided with a high refractive coating.

Examples of particularly suitable inherently high refractive materials are selectively or nonselectively absorbing materials, for example platelet-shaped metal oxides, sulfides and nitrides such as in particular platelet-shaped (semiopaque) α-iron(III) oxide (α-$Fe_2O_3$, hematite), which may be doped with silicon (EP-A-14 382), aluminum (EP-A-68 311) or aluminum and manganese (EP-A-265 820) (eg Paliocrom® Kupfer L3000, BASF; AM200, Titan Kogyo), platelet-shaped (opaque) iron(II/III) oxide ($Fe_3O_4$, magnetite), molybdenum sulfide, boron nitride and graphite platelets. Also suitable are nonabsorbing (colorless) transparent materials such as platelet-shaped bismuth oxychloride, titanium dioxide and zirconium dioxide platelets.

Examples of particularly suitable inherently only low refractive materials are in particular silicatic platelets such as especially light-colored or white micas, preferably wet-ground muscovite, but also other natural micas, for example phlogopite and biotite, artificial micas, talc and glass flakes and silicon dioxide platelets.

The high refractive coating for these low refractive materials may be in particular high refractive metal oxides, metal nitrides and metal sulfides such as titanium oxide, zirconium oxide, zinc oxide and tin oxide, bismuth oxychloride, iron oxides, chromium oxide and ilmenite and also reduced titanium compounds containing titanium having oxidation states of <4 to 2, such as $Ti_3O_5$, $Ti_2O_3$, TiO, titanium oxynitrides and TiN, which are formed on reducing titania-coated substrates with ammonia, hydrogen and/or hydrocarbons. Preference is given not only to ilmenite but in particular to titanium dioxide and its reduction products and also to iron(III) oxide.

Thusly coated mica pigments are likewise commercially available (Paliocrom, BASF; Iriodin®, Merck; Mearlin®, Mearl).

Customary geometric layer thicknesses for these high refractive coatings lie in the range from about 10 to 300 nm, especially in the range from 20 to 200 nm.

The size of the substrate particles may be adapted to the particular application. Generally the platelets have average largest diameters of from about 1 to 200 μm, especially from 5 to 100 μm, and thicknesses from about 0.1 to 1 μm, especially round about 0.5 μm, in the case of metallic substrates and around about 0.3 μm in the case of nonmetallic substrates. Their specific free surface area (BET) is typically in the range from 1 to 15 m²/g, especially from 0.1 to 5 m²/g in the case of metallic and from 1 to 12 m²/g in the case of nonmetallic substrates.

The luster pigments of the invention comprise a low refractive coating (A) which absorbs visible light selectively in combination with a reflective coating (B) which is at least partially transparent to visible light. They may include a plurality of identical or different combinations (layer packets) (A)+(B), but a coating with just one layer packet (A)+(B) is preferred.

The coating (A) according to the invention is preferably constructed from a colorless low refractive material embedding one or more selectively absorbing colorants.

The layer material (A) and correspondingly also the coating (A) preferably has a refractive index n ≦1.8, especially ≦1.6.

The layer material (A) may in principle be any low refractive colorless substance which is capable of being applied to the substrate particles in the form of a durable film.

Examples of particularly suitable substances are metal oxides and metal oxyhydrates such as silicon oxide, silicon oxyhydrate, aluminum oxide, aluminum oxyhydrate, aluminum hydroxide and mixtures thereof, preference being given to (hydrated) silicon oxide.

The preferred coating (A) of the invention includes embedded selectively absorbing colorant. This colorant may be essentially homogeneously dispersed in the coating (A) or concentrated in a region of coating (A), eg in the lower or upper part or in the middle of the layer (A), or the coating (A) may have a concentration gradient with regard to the colorant. Preferably the colorant is concentrated in the lower, substrate-near region of the coating (A).

The colorant may be any dye or pigment capable of being permanently embedded in the layer (A) and having a refractive index which is preferably not significantly above the refractive index of the layer material (A). In principle higher refractive colorants can be used as well, but in that case their level in the coating (A) should not be so high as to markedly raise the refractive index of the coating (A) and reduce the goniochromaticity of the luster pigments according to the invention.

As well as low refractive inorganic pigments such as cyanoferrates (eg K$_3$[Fe(CN)$_6$], K[Fe(II)Fe(III)(CN)$_6$], Fe(III)[Fe(II)Fe(III)(CN)$_6$]), granates (eg Ca$_3$Cr$_2$Si$_3$O$_{12}$), phosphates (especially cobalt phosphates, eg Co$_3$(PO$_4$)$_2$, CoLiPO$_4$), borates (especially cobalt borates, eg (Co,Mg)$_2$B$_2$O$_5$) and ultramarine (eg Na$_4$[Al$_3$Si$_3$O$_{12}$]S$_3$), it is organic pigments which are particularly suitable, since their interaction with light is based on absorption in particular. The following pigment classes may be mentioned by way of example: azo, disazo, anthanthrone, anthraquinone, anthrapyrimidine, quinacridone, quinophthalone, diketopyrrolopyrrole, dioxazine, flavanthrone, indanthrone, isoindoline, isoindolinone, isoviolanthrone, metal complex, perinone, perylene, phthalocyanine, pyranthrone, thioindigo and triarylcarbonium pigments.

Dyes are particularly suitable, since unlike pigments they do not act as scattering centers. Any dye can be used in principle, but preference is given to dyes which are soluble in water and/or in water-miscible organic solvents, eg alcohols, and are therefore advantageous to incorporate into the coating (A) under the reaction conditions customarily used for preparing this layer.

Dyes with high affinity for the layer material (A) are very particularly suitable. In the case of acidic layer material (A), eg silicon dioxide, preference is therefore given to cationic (basic) dyes, while anionic dyes (acid dyes) are preferred in the case of basic layer material (A), eg aluminum oxide. Amphoteric layer materials may be used with either class of dye.

Cationic dyes carry a positive charge which may be delocalized over the dye molecule or localized on a hetero atom, especially a nitrogen atom (quaternary ammonium ion), but also on an oxygen, sulfur or phosphorus atom. The salt-forming counterion is usually the colorless anion of an organic or inorganic acid of low molecular weight.

Examples of useful cationic dyes having a delocalized positive charge are:

methine dyes (vinylogous amidinium salts):
  enamine dyes (one terminal nitrogen atom of the methine chain is part of a heterocyclic ring, the other nitrogen atom is attached directly to the methine chain);
  cyanine dyes (both terminal nitrogen atoms are part of a heterocyclic ring);
  mono- or diazamethine dyes (one or two nitrogen atoms additionally replace carbon atoms in the methine chain);
  diazacyanine dyes (cationic azo dyes)
di- and triarylmethane dyes:
  monomethine dyes having two or three terminal aryl (especially phenyl) radicals where at least one, but preferably two or three, aryl radicals are substituted by an electron-donating group (usually a dialkylamino group) para to the methine carbon atom; eg malachite green and crystal violet
xanthene dyes:
  triphenylmethane dyes having an oxygen atom linking two phenyl rings; eg rhodamine B
azine dyes:
  phenazine dyes (dibenzofused pyrazine);
  phenoxazine dyes (dibenzofused 1,4-oxazine);
  phenothiazine dyes (dibenzofused 1,4-thiazine), eg methylene blue.

Useful cationic dyes having a localized positive charge include in particular dyes which can be described by the formula I:

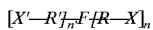

$$[X'{-}R'_{n'}{-}F{-}R{-}X]_n \qquad \text{I}$$

where:
F is the (n+n')-valent radical of a chromophore from the group of the anthanthrones, anthraquinones, anthrapyrimidines, mono-, dis- and polyazo dyes, quinacridones, quinophthalones, diketopyrrolopyrroles, dioxazines and bisdioxazines, flavanthrones, indanthrones, isoindolines, isoindolinones, naphthalimides, perinones, perylenes, terrylenes and quaterrylenes, phthalocyanines, porphyrins, pyranthrones, rhodamines, violanthrones and isoviolanthrones, thioindigo dyes and xanthenes;

R, R' are independently a C$_1$–C$_{10}$-alkylene radical whose carbon chain may be interrupted by oxygen atoms in ether function, in which case ethylene and especially methylene are preferred, or an arylene, hetarylene, aralkylene or hetaralkylene radical, in which case phenylene, naphthylene, pyridylene, methylenephenylene and ethylenephenylene are preferred;

X, X' are independently a univalent positively charged radical, preferably
a radical of the formula Ia

Ia where $R^1$, $R^2$ and $R^3$ are independently $C_1$–$C_{10}$-alkyl, $C_1$–$C_{10}$-alkoxy, aryl or hetaryl, which may each be substituted by one or more hydroxyl or cyano substituents, and where two of $R^1$, $R^2$ and $R^3$ may also be combined with the nitrogen atom to form a 5-, 6- or 7-membered saturated ring attached via the nitrogen atom,
a radical of the formula Ib

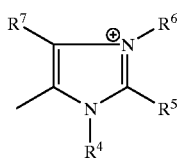
Ib where $R^4$, $R^5$, $R^6$ and $R^7$ are independently hydrogen, $C_1$–$C_4$-alkyl, especially methyl or ethyl, $C_1$–$C_4$-hydroxyalkyl, especially hydroxymethyl or hydroxyethyl, preference being given to Ib radicals in which $R^4$ and $R^6$ are independently methyl, hydroxyethyl or hydrogen, $R^5$ is hydrogen and $R^7$ is methyl or hydrogen, or
a radical of the formulae Ic

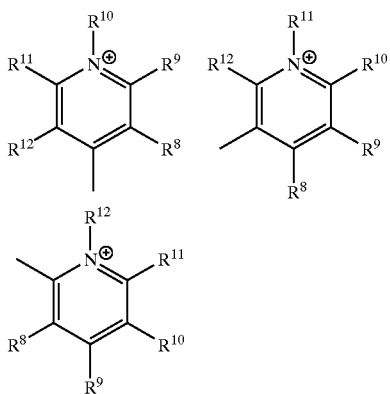
Ic where $R^8$, $R^9$, $R^{10}$, $R^{11}$ and $R^{12}$ are independently selected from the group consisting of hydrogen, $C_1$–$C_4$-alkyl and $C_1$–$C_4$-alkoxy;

n, n' are each from 0 to 4, subject to the proviso that (n+n') is at least 1.

Useful colorless anions include for example halides, especially chloride, sulfate, hydrogen sulfate, phosphate, hydrogen- and dihydrogenphosphate, nitrate, hydroxide, formate, acetate, propionate and benzoate.

The cationic dyes of the formula I are well known. Imidazolylmethylated dyes are described for example in EP-A-335 237 and 643 108.

Useful anionic dyes include in particular anionic dyes which can be described by the formula II:

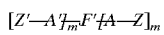
II where:
F' is the (m+m')-valent radical of a chromophore from the group of the anthanthrones, anthraquinones, anthrapyrimidines, mono-, dis- and polyazo dyes, quinacridones, quinophthalones, diketopyrrolopyrroles, dioxazines and bisdioxazines, flavanthrones, indanthrones, isoindolines, isoindolinones, naphthalimides, perinones, perylenes, terrylenes and quaterrylenes, phthalocyanines, porphyrins, pyranthrones, rhodamines, violanthrones and isoviolanthrones, thioindigo dyes and xanthenes;

A, A' are independently a chemical bond, a $C_1$–$C_{10}$alkylene radical whose carbon chain may be interrupted by oxygen atoms in ether function, in which case ethylene and especially methylene are preferred, or an arylene, hetarylene, aralkylene or hetaralkylene radical, in which case phenylene, naphthylene, pyridylene, methylenephenylene and ethylenephenylene are preferred;

Z, Z' are independently a univalent negatively charged radical, preferably a radical of the formulae IIa to IIc

 IIa
 IIb
 IIc m, m' are each from 0 to 6, subject to the proviso that (m+m') is at least 1.

The salt-forming counterion in the anionic dyes is generally a colorless cation, for example a hydrogen cation, alkali metal cation, especially lithium, sodium, potassium cation, alkaline earth metal cation, especially magnesium, calcium cation and ammonium ion.

The anionic dyes of the formula II are likewise well known.

The preferred coating (A) of the invention includes typically from 0.1 to 50% by weight, preferably from 1 to 40% by weight, particularly preferably from 5 to 25% by weight, of colorant.

The geometric layer thickness of coating (A) is generally from 10 to 800 nm, preferably from 100 to 600 nm. Since it is the layer (A) which essentially determines the interference colors of the pigments according to the invention, it has a minimum geometric layer thickness of 100 nm, preferably 200 nm, for luster pigments which include only one layer packet (A)+(B) and exhibit a pronounced color play and are therefore also preferred. If a plurality (eg 2, 3 or 4) of layer packets (A)+(B) are present, the geometric layer thickness of (A) is preferably in the range from 50 to 200 nm.

As the thickness of coating (A) increases, the angle dependence of the hue of the luster pigments according to the invention increases as well. Unlike with known luster pigments, the color of the luster pigments according to the invention is influenced not only by interference but also strongly by absorption. Suitable choice of the colorant provides impressive scope for varying the color play of the luster pigments according to the invention. To enhance the color and make it clearly visible even in application media having a low refractive index, for example paints, the luster pigments of the invention are additionally provided with the coating (B).

The reflecting coating (B) of the luster pigments according to the invention has to be at least partially transparent to visible light, i.e. generally transmit at least 10%, preferably at least 30%, of incident light.

Useful materials for the coating (B) of the invention include not only high refractive materials which absorb visible light not at all, selectively or nonselectively but also low refractive substances which have a high absorption constant (generally ≧4) in the visible wavelength region and which of course also have to be depositable in a durable film.

High refractive materials which are particularly useful for coating (B) include for example metals and metal compounds such as metal oxides, metal nitrides and metal sulfides and their mixtures, which may also include low refractive substances in a minor amount as long as the refractive index n of the mixture, which generally should be n≧2, especially ≧2.4, is not markedly lowered.

Specific examples of particularly useful high refractive layer materials (B) are:

nonabsorbing materials:
  metal oxides such as titanium dioxide, titanium oxyhydrate, zirconium dioxide, zirconium oxyhydrate, tin dioxide, tin oxyhydrate, zinc oxide, zinc oxyhydrate and mixtures thereof, preference being given to titanium dioxide and titanium oxyhydrate and mixtures thereof with up to about 5% by weight of other metal oxides, especially tin dioxide, but also silicon dioxide; bismuth oxychloride; metal sulfides such as zinc sulfide;

selectively absorbing materials:
  metal oxides and nitrides such as particularly preferably iron(III) oxides (α- and γ-$Fe_2O_3$), chromium (III) oxide, titanium(III) oxide and titanium nitrides (TiN and titanium oxynitrides $TiO_xN_y$), the lower titanium oxides and nitrides generally being present in the form of a mixture with titanium dioxide; further bismuth vanadate and molybdenum suboxides (molybdenum blue) and also colorless metal oxide layers "colored" with selectively absorbing colorants, for example metal oxide layers comprising titanium dioxide and zirconium dioxide which have been doped with selectively absorbing metal cations or coated with a colorant-including film;

nonselectively absorbing materials:
  metals which can be deposited by gas phase decomposition of volatile metal compounds, such as particularly preferably molybdenum, preferably iron, tungsten and chromium, also cobalt and nickels and also mixtures thereof, and also metals which can be deposited wet-chemically by reduction of metal salt solutions, such as silver, copper, gold, palladium, platinum and alloys, eg NiP, NiB, NiCo, NiWP, CoP and AgAu; metal oxides such as preferably magnetite ($Fe_3O_4$), also cobalt oxide (CoO, $Co_3O_4$) and vanadium oxide ($VO_2$, $V_2O_3$) and also mixtures of these oxides with the metals, eg magnetite/iron; metal sulfides such as particularly preferably molybdenum sulfide, preferably iron sulfide, tungsten sulfide and chromium sulfide, also cobalt sulfide and nickel sulfide and also mixtures of these sulfides such as $MoS_2/WS_2$ and especially also mixtures of these sulfides with the respective metal, eg $MoS_2$/molybdenum, and mixtures with oxides of the respective metal, eg $MoS_2$/molybdenum oxides; carbon.

Useful low refractive, but strongly absorbing layer materials (B) are in particular nonselectively absorbing materials such as metals, for example aluminum.

The geometric layer thickness of coating (B) varies as a function of the optical properties of the selected layer material and can be from 1 to about 500 nm. Preferred geometric layer thicknesses range from 5 to 50 nm, especially from 10 to 40 nm, in the case of high refractive nonabsorbing materials (B) and from 1 to 500 nm, especially from 10 to 150 nm, in the case of high refractive selectively absorbing materials (B). The geometric layer thickness of high refractive nonselectively absorbing materials (B) is preferably in the range from 1 to 100 nm, particularly preferred layer thicknesses ranging from 1 to 25 nm in the case of strongly absorbing metals such as molybdenum and chromium, from 10 to 50 nm in the case of less strongly absorbing materials such as magnetite and from 5 to 20 nm in the case of metal sulfide materials such as $MoS_2$ layers. In the case of low refractive strongly absorbing materials (B) the geometric layer thickness is finally preferably in the range from 1 to 25 nm, particularly preferably from 5 to 20 nm.

When the luster pigments of the invention include a plurality of layer packets (A)+(B), the layer thickness of the (B) coatings is customarily less by from about 50 to 75%.

The coating (B) enhances the color play of the luster pigments coated with the coating (A), may modify it (for example by selective absorption) and makes it clearly visible in all application media. As explained above, the color play of the luster pigments coated with (A) (and (B)) is specifically variable through the choice of colorant incorporated in coating (A).

When, for example, a platelet-shaped aluminum pigment is coated with a silicon dioxide layer about 350 nm in thickness and a semitransparent molybdenum layer (B), a plan view shows the applied pigment to exhibit a vigorous green, which flops toward blue at steeper viewing angles. By incorporating a blue colorant in the silicon dioxide layer, the hue range of the bluish green shades in the color play of the pigment may be advantageously escalated so that the pigment is turquoise in plan view and blue at steeper viewing angles.

This effect is even more impressive for example in the case of an aluminum pigment likewise coated with a silicon dioxide layer about 350 nm in thickness, but with an iron(III) oxide layer (B) instead of the molybdenum layer. Before the selectively absorbing colorant is incorporated, the pigment has a greenish golden color, which becomes achromatic at steeper viewing angles. The incorporation of a blue colorant in the silicon dioxide layer brings about an intensively green color in plan view and a flop into bluish green at steeper viewing angles.

Finally the luster pigments of the invention may additionally include an outer layer (C), especially to protect layers (B) underneath which essentially include metallic or reduced (low-valent) metal oxides.

The layer (C) can be constructed from low refractive or high refractive metal oxides, which can be not only colorless but also selectively absorbing. Examples of useful metal oxides are silicon oxide, silicon oxyhydrate, aluminum oxide, aluminum oxyhydrate, tin oxide, titanium dioxide, zirconium oxide, iron(III) oxide and chromium(III) oxide, of which silicon oxide and aluminum oxide are preferred.

The layer (C) may also be an $SiO_2$-containing layer which is to be obtained by gas phase passivation, which contains phosphate, chromate and/or vanadate and also phosphate and aminoalkyl groups and which in particular makes possible the use in waterborne coatings or other aqueous systems of the luster pigments according to the invention which include a substantially metallic layer (B).

The geometric thickness of layer (C) is generally from about 1 to 400 nm, preferably from 5 to 250 nm.

The luster pigments of the invention are notable for the uniform, homogeneous and filmlike construction of the interference-capable coating which surrounds the substrate platelets on all sides. They exhibit a very strong, extremely angle-dependent color play with novel color flops and high brilliance, which can be specifically adapted to the particular coloristic requirements.

The luster pigments of the invention can be prepared with advantage by applying the preferred, colorant-containing coating (A) wet-chemically to the substrate particles by hydrolytic decomposition of organic or inorganic metal compounds in the presence of the colorant and depositing the coating (B) (and also if desired the coating (C)) subsequently likewise wet-chemically or preferably via gas phase decomposition of volatile metal compound (chemical vapor deposition, CVD).

Depending on the distribution desired for the colorant in the coating (A), the first coating step is advantageously carried out as follows:

If the colorant is to be essentially homogeneously dispersed in the coating (A), the metal compound to be decomposed and the colorant (optionally as a solution) are metered simultaneously into the suspension of the substrate particles. If the colorant is to be concentrated in the upper part of the coating (A), initially only the metal compound to be decomposed is metered in and the metered addition of the colorant is not started until sufficient layer material (A) has already been deposited on the substrate particles. If the colorant is to be conversely concentrated in the lower part of the coating (A), then the substrate particles and the colorant are initially charged and the metal compound to be decomposed is then metered in. The concentration of free colorant in the pigment suspension then decreases with increasing coating.

When the coating (A) is deposited on the basis of organic metal compounds, which variant is preferred in the case of metallic substrate particles in particular, one advantageous way of proceeding is in accordance with the process described in EP-A-668 329, wherein organic silicon and/or aluminum compounds in which the organic radicals are attached to the metals via oxygen atoms are hydrolyzed in the presence of the substrate particles and of an organic solvent in which the metal compounds are soluble and which is miscible with water.

The preferred embodiment here comprises hydrolyzing the metal alkoxides (especially tetraethoxysilane and aluminum triisopropoxide) in the presence of an alcohol (especially isopropanol or ethanol) and of aqueous ammonia as catalyst.

The process is preferably carried out by initially charging substrate particles, alcohol, water and ammonia, heating this mixture to from 40 to 80° C., especially from 60 to 70° C., with stirring and continuously metering in a solution of the metal alkoxide in alcohol. At the same time, the colorant is added as described above in a manner appropriate for the desired distribution in the layer (A) (homogeneous or regionally concentrated). Following a subsequent stirring time of usually from about 1 to 15 h, the mixture is cooled down to room temperature and the coated pigment is isolated by filtration and drying.

Silicon oxide (or oxyhydrate) coatings (A) may advantageously also be produced starting from alkali metal silicates, especially sodium silicate.

An advantageous procedure is described in prior German Patent Application 198 08 657.1. The (preferably nonmetallic) substrate particles are suspended in water, the suspension is heated to from about 20 to 100° C., preferably from 40 to 80° C., adjusted with a base (especially an alkali metal hydroxide solution such as potassium hydroxide solution or sodium hydroxide solution) or an acid (eg nitric acid) to a pH which is generally within the range from 4 to 9, preferably from 6.5 to 8.5, especially about 7.5, and the alkali metal silicate solution is metered in at the same time as an aqueous inorganic acid is added to keep the pH constant. Here too the colorant is added depending on the desired coating outcome (initially charging it together with the substrate particles, metering it at the same time as the alkali metal silicate or adding it later). If desired, the mixture is subsequently stirred for from a few min to 2 h.

The coatings (B) (and optionally (C)) according to the invention may be deposited with advantage by the CVD process or likewise wet-chemically.

The CVD variant employs as starting compounds volatile metal compounds, especially metal carbonyls, metal alkoxides, organometallics or metal halides, which decompose in a temperature range from about 100 to 600° C. in the presence of inert gas, air or water vapor inertly, oxidatively or hydrolytically into metal or metal oxide films which deposit on the pigment particles and which may subsequently be converted into metal sulfide or metal nitride films by reaction with sulfur-containing compounds or ammonia-containing gases.

The wet-chemical variant is particularly useful for producing metal oxide coatings (B), especially titanium dioxide coatings, and is preferably based on the hydrolytic decomposition of suitable metal salts or alkoxides.

Both process variants are well known. Details may be found in EP-A-753 545 and prior German Patent Application 198 08 657.1.

The luster pigments of the invention are very useful for many purposes, such as coloration of glasses, ceramic products, decorative cosmetic preparations and especially paints, inks, including printing inks, especially security printing inks, and plastics. Printing may be effected by any industrially customary printing processes, for example screen printing, intaglio printing, bronze printing, flexographic printing and offset printing.

The pigments of the invention may also be used with advantage for these purposes in a blend with transparent and hiding white, color and black pigments and also conventional luster pigments based on metal oxide-coated mica and metal pigments and known goniochromatic luster pigments.

EXAMPLES

Preparation of Luster Pigments According to the Invention

Example 1 a) 120 g of a 65% by weight aluminum paste (average particle size about 16 μm; Alpate® 7670 NS, Alcan Toyo) were slurried up in 1.5 l of isopropanol. After 15 minutes of stirring, 160 g of a 25% by weight solution of the dye of the formula I' (CuPc: copper phthalocyanine)

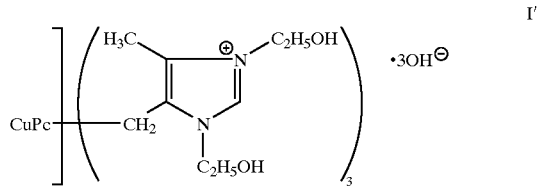

in 3% by weight aqueous acetic acid, 400 ml of water and 40 ml of 25% by weight aqueous ammonia solution were added in succession. While simultaneously heating to 60°

C., the parallel metered addition was commenced of a mixture of 680 g of tetraethoxysilane and 680 g of isopropanol and also 125 ml of 2.5% by weight aqueous ammonia solution (metering time 24 h). After a subsequent stirring time of 2 h and cooling of the suspension down to room temperature, the product was filtered off, washed with isopropanol and dried at 70° C.

This afforded 310 g of an intensively turquoise blue pigment.

b) 200 g of the pigment obtained in step a) were subsequently heated to 200° C. in a fluidized bed reactor under fluidization with a total of 1000 l/h of nitrogen. 40 g of molybdenum hexacarbonyl were then transferred with a portion of the fluidizing gases (400 l/h) from a feed vessel temperature controlled to 80° C. in about 8 h into the reactor, where they were decomposed into carbon monoxide and molybdenum which deposited onto the (A)-coated pigment particles. After the deposition of molybdenum was complete, some air was added to the fluidizing gases to passivite the molybdenum surface in the course of the reactor cooling down.

The pigment obtained had a silicon content of 24.2% by weight, a carbon content of 8.9% by weight and a molybdenum content of 4.7% by weight. On application, a plan view showed it to have a vigorous bluish green interference color which flopped toward blue with an increasingly inclined view.

Example 2 a) Step a) of Example 1 was repeated four times to produce a total of 1.2 kg of the aluminum pigment coated with silicon dioxide containing blue dye.

b) 1000 g of the pigment obtained in step a) were subsequently heated to 200° C. in a fluidized bed reactor under fluidization with a total of 1950 l/h of nitrogen. A portion of the fluidizing gases (300 l/h) was then passed into the reactor via a feed vessel which was temperature controlled to 30° C. and contained 150 g of iron pentacarbonyl, while another portion of the fluidizing gases (150 l/h) was saturated with water vapor (60 ml/h of water). An additional 300 l/h of air were introduced through a further reactor opening. After about 8 h the entire carbonyl had been transferred into the reactor and had decomposed into $\alpha$-$Fe_2O_3$ which deposited on the (A)-coated pigment particles.

The pigment obtained had a silicon content of 25.5% by weight, a carbon content of 8.9% by weight and a iron content of 2.9% by weight. On application, a plan view showed it to have a vigorous yellowish green interference color which flopped into bluish green with an increasingly inclined view.

Example 3 a) Step a) of Example 1 was repeated four times to produce a total of 1.2 kg of the aluminum pigment coated with silicon dioxide containing blue dye.

b) 1000 g of the pigment obtained in step a) were subsequently heated to 200° C. in a fluidized bed reactor under fluidization with a total of 1800 l/h of nitrogen. A portion of the fluidizing gases (400 l/h) was then passed through a water feed vessel temperature controlled to 50° C. and a further portion of the fluidizing gases (400 l/h) was passed through a feed vessel temperature controlled to 120° C. and containing a mixture of titanium tetraethoxide and titanium tetraisopropoxide in a molar ratio of 1:1 (Titanat IPET, from Hüls). In the course of about 8 h, 150 ml of the titanium tetraalkoxide mixture were thus transferred into the reactor a little at a time and decomposed into $TiO_2$ which deposited on the (A)-coated pigment particles.

The pigment obtained had a silicon content of 25.8% by weight, a carbon content of 8.9% by weight and a titanium content of 2.2% by weight. On application, a plan view showed it to have a vigorous turquoise hue which flopped toward blue with an increasingly inclined view.

Example 4 a) 130 g of the titania-coated mica pigment (Iriodin® Sterling Silber 103; Merck) were suspended in 1 l of water. After 15 minutes of stirring, 250 g of a 25% by weight solution of the dye of the formula I' of Example 1 in 3% by weight of aqueous acetic acid were added. After the suspension had been heated to 75° C., 1540 ml of sodium silicate solution (68 g Si/l) were added in the course of about 48 h, during which the pH of the suspension was maintained at 8.8 by simultaneous addition of 416 ml of 20% by weight nitric acid. Following a subsequent stirring time of 1 h and cooling down to room temperature, the product was filtered off, washed with water and with ethanol and subsequently dried at 75° C. under reduced pressure.

This afforded 429 g of a blue pigment.

Step a) was repeated a further two times to produce in total about 1.2 kg of the mica pigment coated with silicon dioxide containing blue dye.

b) 1000 g of the pigment obtained in step a) were subsequently coated with titanium dioxide similarly to Example 3b).

The pigment obtained had a silicon content of 27.3% by weight, a carbon content of 8.0% by weight and a titanium content of 6.9% by weight. On application, a plan view showed it to have a vigorous greenish blue interference color which flopped toward dark blue with an increasingly inclined view.

What is claimed is:

1. Luster pigments based on multiply coated reflecting platelet-shaped substrates and comprising at least one layer packet comprising
   A) a low refractive coating which selectively absorbs visible light and has a refractive index $n \leq 1.8$ and
   B) a reflective coating which is at least partially transparent to visible light and also, if desired,
   C) an outer protective layer.

2. Luster pigments as claimed in claim 1, wherein the substrate comprises metallic or high refractive nonmetallic platelets having a refractive index $\geq 2$, which each already has been optionally coated with a high refractive layer, or low refractive nonmetallic platelets which are already coated with a high refractive layer.

3. Luster pigments as claimed in claim 1, wherein the coating (A) comprises a colorless low refractive material embedding one or more selectively absorbing colorants.

4. Luster pigments as claimed in claim 3, wherein the colorant is substantially homogeneously dispersed in the coating (A) or concentrated in a region of coating (A).

5. Luster pigments as claimed in claim 1, wherein the coating (A) includes a cationic dye.

6. Luster pigments as claimed in claim 1, wherein the coating (A) has a geometric thickness of from 100 to 800 nm.

7. Luster pigments as claimed in claim 1, wherein the coating (B) comprises high refractive materials which absorb visible light not at all or selectively or nonselectively or low refractive materials which strongly absorb visible light.

8. Luster pigments as claimed in claim 1, wherein the coating (B) has a refractive index $n \geq 2$ and/or an absorption constant $k \geq 4$.

9. A method of coloring paints, inks, plastics, glasses, ceramic products or decorative cosmetic preparations which comprises incorporating the luster pigments of claim 1 therein.

* * * * *